(12) United States Patent
Dewerchin et al.

(10) Patent No.: US 8,293,464 B2
(45) Date of Patent: Oct. 23, 2012

(54) METHODS FOR REDUCING THE INTERNALIZATION OF VIRUSES AND IDENTIFICATION OF COMPOUNDS EFFECTIVE THEREOF

(75) Inventors: Hannah Dewerchin, Merelbeke (BE); Hans Nauwynck, Merelbeke (BE)

(73) Assignee: Universiteit Gent, Ghent (BE)

( * ) Notice: Subject to any disclaimer, the term of this patent is extended or adjusted under 35 U.S.C. 154(b) by 0 days.

(21) Appl. No.: 12/996,453

(22) PCT Filed: May 29, 2009

(86) PCT No.: PCT/EP2009/003865
§ 371 (c)(1),
(2), (4) Date: Mar. 22, 2011

(87) PCT Pub. No.: WO2009/146859
PCT Pub. Date: Dec. 10, 2009

(65) Prior Publication Data
US 2011/0190273 A1    Aug. 4, 2011

(30) Foreign Application Priority Data

Jun. 2, 2008 (GB) .................................. 0809898.0

(51) Int. Cl.
*C12Q 1/00* (2006.01)
*C12Q 1/70* (2006.01)
*A01N 61/00* (2006.01)
*A61K 31/00* (2006.01)
*A61K 38/00* (2006.01)

(52) U.S. Cl. ....................... 435/4; 435/5; 514/1; 514/1.1

(58) Field of Classification Search .......................... None
See application file for complete search history.

(56) References Cited

FOREIGN PATENT DOCUMENTS
EP         0 610 519 A1    8/1994
WO      2007/062063 A2    5/2007

OTHER PUBLICATIONS

Aderem et al., "Mechanisms of Phagocytosis in Macrophages", Annu. Rev. Immunol. 17, pp. 593-623, 1999.
Dewerchin et al., "Feline infectious peritonitis virus-infected monocytes internalize viral membrane-bound proteins upon antibody addition", Journal of General Virology 67, pp. 1685-1690, 2006.
Dewerchin et al., "Surface-expressed viral proteins in feline infectious peritonitis virus-infected monocytes are internalized through a clathrin- and caveolae-independent pathway", Journal of General Virology, 89, pp. 2731-2740, 2008.
Dewerchin, "Characterization of putative immune evasion mechanisms of feline infectious peritonitis virus", Thesis, 1996.
Gallagher et al., "Myosin light chain kinases", Journal of Muscle Research and Cell Motility, 18, pp. 1-16, 1997.

Guerriero et al., "Production and Characterization of an Antibody to Myosin Light Chain Kinase and Intracellular Localization of the Enzyme", Cell, vol. 27, pp. 449-458, Dec. 1981.
Imberechts et al., "Characterization of F107 Fimbriae of *Escherichia coli* 107/86, Which Causes Edema Disease in Pigs, nad Nucleotide Sequence of F107 Major Fimbrial Subunit Gene, fedA", Infection and Immunity, vol. 60, No. 5, pp. 1963-1971, May 1992.
Imberechts et al., Characterization of F18 fimbrial genes fedE and fedF involved in adhesion and length of enterotoxemic *Escherichia coli* strain 107/86.
Yu-Hua Liu et al., "Distribution of H Type 1 and of H Type 2 Antigens of ABO Blood Group in Different Cells of Human Submandibular Gland", Journal of Histochemistry & Cytochemistry, 46:69, 1998.
McArdle et al., "Induction and enhancement of feline infectious peritonitis by canine coronavirus", Am J. Vets Res, vol. 53, No. 9, Sep. 1992.
McKeirnan et al., "Isolation of Feline Coronaviruses from Two Cats with Diverse Disease Manifestations", Feline Practice—Medicine, vol. 11, No. 3., Jun. 1981.
O'Hara et al., "Myosin II-Dependent Membrane Translocation of SGLTI and Aqpl Is Required for Efficient *C. parvum* Cellular Invasion of Cholangiocytes", 2008.
Pedersen et al., "Immunologic Phenomena in the Effusive Form of Feline Infectious Peritonitis", Am J Vet Res, vol. No. 6, pp. 868-876, 1980.
Pedersen et al., "Attempted immunization of cats against feline infectious peritonitis, using avirulent live virus or sublethal amounts of virulent virus", American Journal of Veterinary Research, vol. 44, No. 2, pp. 229-234, Feb. 1983.
Petrache et al., "Caspase-dependent cleavage of myosin light chain kinase (MLCK) is involved in TNF—mediated bovine pulmonary endothelial cell apoptosis", The FASEB Journal, vol. 17, Mar. 2003.
Ruiz-Palacious et al., "Campylobacter jejuni Binds Intestinal H(O) Antigen (fucα1, 2GAIβ1, 4G1cNAc), and Fucosyloligosaccharides of Human Milk Inhibit Its Binding and Infection", The Journal of Biological Chemistry, vol. 278, No. 16, pp. 14112-14120, Issue of Apr. 18, 2003.
Saitoh et al., "Selective Inhibition of Catalytic Activity of Smooth Muscle Myosin Light Chain Kinase", The Journal of Biological Chemistry, vol. 262, No. 16, pp. 7796-7801, Issue of Jun. 5, 1987.

(Continued)

*Primary Examiner* — Robert Landsman
(74) *Attorney, Agent, or Firm* — Dinsmore & Shohl LLP

(57) ABSTRACT

The invention relates generally to the field of virology, and relates to the identification and characterization of the targets involved in the evasion strategy of viruses and to the use thereof in methods to identify anti-viral compounds. More in particular to identify compounds which are modulators of myosin light chain kinase (MLCK), a target within said entry and immune-evasion strategy. Other aspects of the invention are directed to anti-viral compounds identified using the models and methods of the present invention, as well as to the use thereof in treating viral infections, such as for example caused by the feline infectious peritonitis virus (FIPV), a coronavirus which belongs to an antigenic group which comprises in particular feline enteric coronavirus (FECV), canine coronavirus (CCV), swine transmissible gastroenteritis coronavirus (TGEV), porcine respiratory coronavirus (PRCV) and human coronavirus (HCV), and which induces, in a host-dependent manner, a range of symptoms which range from mild enteritis to the severe debilitating disease, and, in some cases, up to death. In a particular aspect the present invention provides the use of MLCK inhibitors for the treatment of feline infectious peritonitis (FIP).

8 Claims, 8 Drawing Sheets

OTHER PUBLICATIONS

Sato et al., "Inhibition of Human Immunodeficiency Virus Type 1 Replication by a Bioavailable Serine/Threonine Kinase Inhibitor, Fasudil Hydrochloride", Aids Research and Human Retroviruses, vol. 14, No. 4, 1998.

Tiels et al., "The excretion of F18+ *E. coli* is reduced after oral immunisation of pigs with a FedF and F4 fimbriae conjugate", Vaccine 26, pp. 2154-2163, 2008.

Totsukawa et al., "Distinct Roles of ROCK (Rho-kinase) and MLCK in Spatial Regulation of MLC Phosphorylation for Assembly of Stress Fibers and Focal Adhesions in 3T3 Fibroblasts", The Journal of Cell Biology, vol. 150, No. 4, pp. 797-806, Aug. 21, 2000.

Vennema et al., "Early Death after Feline Infectious Peritonitis Virus Challenge due to Recombinant Vaccinia Virus Immunization", Journal of Virology, vol. 64, No. 3, pp. 1407-1409, Mar. 1990.

Verdonck et al., "Different kinetic of antibody responses following infection of newly weaned pigs with an F4 enterotoxigenic *Escherichia coli* strain or an F18 verotoxigenic *Escherichia coli* strain", Vaccine 20, pp. 2995-3004, 2002.

Ydrenius et al., "Activation of cAMP-dependent protein kinase is necessary for actin rearrangements in human neutrophils during phagocytosis", Journal of Leukocyte Biology, vol. 67, Apr. 2000.

Young-Sook Kim et al., "Studies on the Antiviral Mechanisms of Protein Kinase Inhibitors K-252a and KT5926 against the Replication of Vesicular Stomatitis Virus", Biol. Pharm. Bull 21(5), pp. 498-505, 1998.

International Search Report for PCT/EP2009/003865 dated Jan. 28, 2010.

Imberechts et al., Characterization of F18 fimbrial genes fedE and fedF involved in adhesion and length of enterotoxemic *Escherichia coli* strain 107/86, Microbial Pathogenesis, 21:183-192, 1996.

SEQUENCE LISTING

```
<160> NUMBER OF SEQ ID NOS: 2

<210> SEQ ID NO 1
<211> LENGTH: 1415
<212> TYPE: DNA
<213> ORGANISM: Homo Sapiens

<400> SEQUENCE: 1
actgaacaaa aagtatctga cttctacgac attgaggaga gattaggatc tgggaaattt      60
ggacaggtct ttcgacttgt agaaaagaaa actcgaaaag tctgggcagg gaagttcttc     120
aaggcatatt cagcaaaaga gaaagagaat atccggcagg agattagcat catgaactgc     180
```

```
ctccaccacc ctaagctggt ccagtgtgtg gatgcctttg aagaaaaggc caacatcgtc      240
atggtcctgg agatcgtgtc aggaggggag ctgtttgagc gcatcattga cgaggacttt      300
gagctgacgg agcgtgagtg catcaagtac atgcggcaga tctcggaggg agtggagtac      360
atccacaagc agggcatcgt gcacctggac ctcaagccgg agaacatcat gtgtgtcaac      420
aagacgggca ccaggatcaa gctcatcgac tttggtctgg ccaggaggct ggagaatgcg      480
gggtctctga aggtcctctt tggcacccca gaatttgtgg ctcctgaagt gatcaactat      540
gagcccatcg gctacgccac agacatgtgg agcatcgggg tcatctgcta catcctagtc      600
agtggccttt cccccttcat gggagacaac gataacgaaa ccttggccaa cgttacctca      660
gccacctggg acttcgacga cgaggcattc gatgagatct ccgacgatgc caaggatttc      720
atcagcaatc tgctgaagaa agatatgaaa accgcctgg actgcacgca gtgccttcag      780
catccatggc taatgaaaga taccaagaac atggaggcca gaaactctc caaggaccgg      840 atgaagaagt acatggcaag aaggaaatgg cagaaaacgg gcaatgctgt gagagccatt      900
ggaagactgt cctctatggc aatgatctca gggctcagtg caggaaaatc ctcaacaggg      960
tcaccaacca gcccgctcaa tgcagaaaaa ctagaatctg aagatgtgtc ccaagctttc     1020
cttgaggctg ttgctgagga aaagcctcat gtaaaaccct atttctctaa gaccattcgc     1080
gatttagaag ttgtggaggg aagtgctgct agatttgact gcaagattga aggatacccca     1140 gaccccgagg ttgtctggtt caaagatgac cagtcaatca gggagtcccg ccacttccag     1200
atagactacg atgaggacgg gaactgctct ttaattatta gtgatgtttg cggggatgac     1260
gatgccaagt acacctgcaa ggctgtcaac agtcttggag aagccacctg cacagcagag     1320
ctcattgtgg aaacgatgga ggaaggtgaa ggggaagggg aagaggaaga agagtgaaac     1380
aaagccagag aaaagcagtt tctaagtcat attaa                                1415
```

<210> SEQ ID NO 2
<211> LENGTH: 458
<212> TYPE: PRT
<213> ORGANISM: Homo Sapiens

<400> SEQUENCE: 2

```
Thr Glu Gln Lys Val Ser Asp Phe Tyr Asp Ile Glu Glu Arg Leu Gly
1               5                   10                  15

Ser Gly Lys Phe Gly Gln Val Phe Arg Leu Val Glu Lys Lys Thr Arg
            20                  25                  30

Lys Val Trp Ala Gly Lys Phe Phe Lys Ala Tyr Ser Ala Lys Glu Lys
        35                  40                  45

Glu Asn Ile Arg Gln Glu Ile Ser Ile Met Asn Cys Leu His His Pro
    50                  55                  60

Lys Leu Val Gln Cys Val Asp Ala Phe Glu Glu Lys Ala Asn Ile Val
65                  70                  75                  80

Met Val Leu Glu Ile Val Ser Gly Gly Glu Leu Phe Glu Arg Ile Ile
                85                  90                  95

Asp Glu Asp Phe Glu Leu Thr Glu Arg Glu Cys Ile Lys Tyr Met Arg
            100                 105                 110

Gln Ile Ser Glu Gly Val Glu Tyr Ile His Lys Gln Gly Ile Val His
        115                 120                 125

Leu Asp Leu Lys Pro Glu Asn Ile Met Cys Val Asn Lys Thr Gly Thr
    130                 135                 140

Arg Ile Lys Leu Ile Asp Phe Gly Leu Ala Arg Arg Leu Glu Asn Ala
145                 150                 155                 160
```

-continued

```
Gly Ser Leu Lys Val Leu Phe Gly Thr Pro Glu Phe Val Ala Pro Glu
            165                 170                 175
Val Ile Asn Tyr Glu Pro Ile Gly Tyr Ala Thr Asp Met Trp Ser Ile
            180                 185                 190
Gly Val Ile Cys Tyr Ile Leu Val Ser Gly Leu Ser Pro Phe Met Gly
            195                 200                 205
Asp Asn Asp Asn Glu Thr Leu Ala Asn Val Thr Ser Ala Thr Trp Asp
            210                 215                 220
Phe Asp Asp Glu Ala Phe Asp Glu Ile Ser Asp Asp Ala Lys Asp Phe
225                 230                 235                 240
Ile Ser Asn Leu Leu Lys Lys Asp Met Lys Asn Arg Leu Asp Cys Thr
            245                 250                 255
Gln Cys Leu Gln His Pro Trp Leu Met Lys Asp Thr Lys Asn Met Glu
            260                 265                 270
Ala Lys Lys Leu Ser Lys Asp Arg Met Lys Lys Tyr Met Ala Arg Arg
            275                 280                 285
Lys Trp Gln Lys Thr Gly Asn Ala Val Arg Ala Ile Gly Arg Leu Ser
    290                 295                 300
Ser Met Ala Met Ile Ser Gly Leu Ser Gly Arg Lys Ser Ser Thr Gly
305                 310                 315                 320
Ser Pro Thr Ser Pro Leu Asn Ala Glu Lys Leu Glu Ser Glu Asp Val
            325                 330                 335
Ser Gln Ala Phe Leu Glu Ala Val Ala Glu Glu Lys Pro His Val Lys
            340                 345                 350
Pro Tyr Phe Ser Lys Thr Ile Arg Asp Leu Glu Val Val Glu Gly Ser
            355                 360                 365
Ala Ala Arg Phe Asp Cys Lys Ile Glu Gly Tyr Pro Asp Pro Glu Val
            370                 375                 380
Val Trp Phe Lys Asp Asp Gln Ser Ile Arg Glu Ser Arg His Phe Gln
385                 390                 395                 400
Ile Asp Tyr Asp Glu Asp Gly Asn Cys Ser Leu Ile Ile Ser Asp Val
            405                 410                 415
Cys Gly Asp Asp Asp Ala Lys Tyr Thr Cys Lys Ala Val Asn Ser Leu
            420                 425                 430
Gly Glu Ala Thr Cys Thr Ala Glu Leu Ile Val Glu Thr Met Glu Glu
            435                 440                 445
Gly Glu Gly Glu Gly Glu Glu Glu Glu
    450                 455
```

METHODS FOR REDUCING THE INTERNALIZATION OF VIRUSES AND IDENTIFICATION OF COMPOUNDS EFFECTIVE THEREOF

FIELD OF THE INVENTION

The invention relates generally to the field of virology, and relates to the identification and characterization of the targets involved in the entry process and immune-evasion strategy of viruses and to the use thereof in methods to identify anti-viral compounds. More in particular to identify compounds which are modulators of myosin light chain kinase (MLCK), a target involved in the internalization and the immune-evasion strategy of viruses, in particular of corona viral infections.

Other aspects of the invention are directed to anti-viral compounds identified using the models and methods of the present invention, as well as to the use thereof in treating corona viral infections, such as for example caused by the feline infectious peritonitis virus (FIPV), which belongs to an antigenic group which comprises in particular feline enteric coronavirus (FECV), canine coronavirus (CCV), swine transmissible gastroenteritis coronavirus (TGEV), porcine respiratory coronavirus (PRCV) and human coronavirus (HCV), and which induces, in a host-dependent manner, a range of symptoms which range from mild enteritis to the severe debilitating disease, and, in some cases, up to death.

In a particular aspect the present invention provides the use of MLCK inhibitors for the treatment of feline infectious peritonitis (FIP).

BACKGROUND TO THE INVENTION

Coronaviruses may cause disease in humans (e.g. the severe acute respiratory syndrome, SARS) and in animals. Coronaviruses primarily infect the upper respiratory and gastrointestinal tract of mammals and birds. Four to five different currently known strains of coronaviruses infect humans. The most publicized human coronavirus, SARS-CoV which causes SARS, has a unique pathogenesis because it causes both upper and lower respiratory tract infections and can also cause gastroenteritis. Coronaviruses are believed to cause a significant percentage of all common colds in human adults. Coronaviruses cause colds in humans primarily in the winter and early spring seasons. The significance and economic impact of coronaviruses as causative agents of the common cold are hard to assess because, unlike rhinoviruses (another common cold virus), human coronaviruses are difficult to grow in the laboratory.

Coronaviruses also cause a range of diseases in farm animals and domesticated pets, some of which can be serious and are a threat to the farming industry. Economically significant coronaviruses of farm animals include porcine coronavirus (transmissible gastroenteritis, TGE) and bovine coronavirus, which both result in diarrhea in young animals. Feline enteric coronavirus is a pathogen of minor clinical significance, but spontaneous mutation of this virus can result in feline infectious peritonitis (FIP), a disease associated with high mortality. In cats, two coronaviruses are described: feline enteric coronavirus (FECV) and feline infectious peritonitis virus (FIPV). These coronaviruses are spread world-wide and infect not only domestic cats but also all other members of the Felidae family. An infection with FIPV causes a severe pleuritis/peritonitis which mostly leads to death. Ill cats usually have very high titers of FIPV-specific antibodies. However, these antibodies are not able to block infection even though infected target cells, blood monocytes, do express viral proteins in their plasma membrane allowing antibody-dependent complement mediated cell lysis. Also cell mediated immunity is impaired as cytotoxic T-cells are depleted during infection. Moreover, some vaccines against feline coronaviruses have been proven to enhance disease when vaccinated animals were exposed to the wild-type virus, and thus anti-body enhancement of disease is a potential risk of coronavirus diseases in animals or humans (Pedersen, N. and Boyle, J. (1980)., Vennema, H. et al. (1990a)., Pedersen, N. and Black, J. (1983) McArdle, F., et al. (1992)).

Drugs with proven efficacy against coronaviruses are currently missing, and there is a clear need to develop effective drugs against coronaviruses. It is accordingly an object of the present invention to provide models and methods to come and identify anti-coronaviral drugs, as well as to the use thereof in treating corona viral infections, such as for example caused by the feline infectious peritonitis virus (FIPV), and in particular in the treatment of FIP.

It has now surprisingly been found that MLCK is involved as a positive regulator in the internalization pathway of viral particles or of viral proteins upon binding of anti-viral antibodies in the host cell, and accordingly an important element in the viral infection pathways. As demonstrated in the examples hereinafter, it has now been found that using specific MLCK inhibitors it is possible to interfere with the internalization of viruses in the host and with the internalization of viral proteins upon binding of anti-viral antibodies in the host cell. The latter is an immune evasion process by which the infected cells can hide itself from the immune system of the host.

Where it has previously been shown that kinase inhibitors can interfere with the viral replication of Rhabdoviridae (Kim Young-Sook and Kawai Akihiko, (1998)), with for example no observed effect in the replication of Togaviridae, said earlier disclosure did not suggest MLCK as a target for inhibitors directed against the aforementioned internalization processes. The present finding accordingly provides a novel anti-viral treatment, which is particularly useful in treating viral infections of virus families selected from the group consisting of Coronaviridae, Nidovirales, Herpesviridae, Orthomyxoviridae, Retroviridae, and Flaviviridae; in particular in the treatment of viral infection of Coronaviridae such as for example caused by the feline infectious peritonitis virus (FIPV) or the feline enteric coronavirus (FECV).

BRIEF DESCRIPTION OF THE DRAWINGS

FIG. 2 Further characterization of the internalization pathway of surface expressed viral antigens in FIPV infected monocytes by inhibiting phosphate transfer during internalization. The activity of each inhibitor was tested with an internalization assay of a suitable control. Results are given relatively to a control of untreated cells. The black bars represent the internalization of the viral antigens. The gray bars represent the internalization of the control ligand (beads, transferrin or albumin). Data are means and standard deviations of triplicate assays. The asterisk marks results that are significantly different from the untreated control ($p<0.05$).

DESCRIPTION OF THE INVENTION

This invention is based on the molecular characterization of the immune-evasion pathway of viruses, i.e. the internalization of membrane-bound viral proteins upon binding with virus specific antibodies, such as for example seen in FIPV-infected monocytes.

Figure 1:
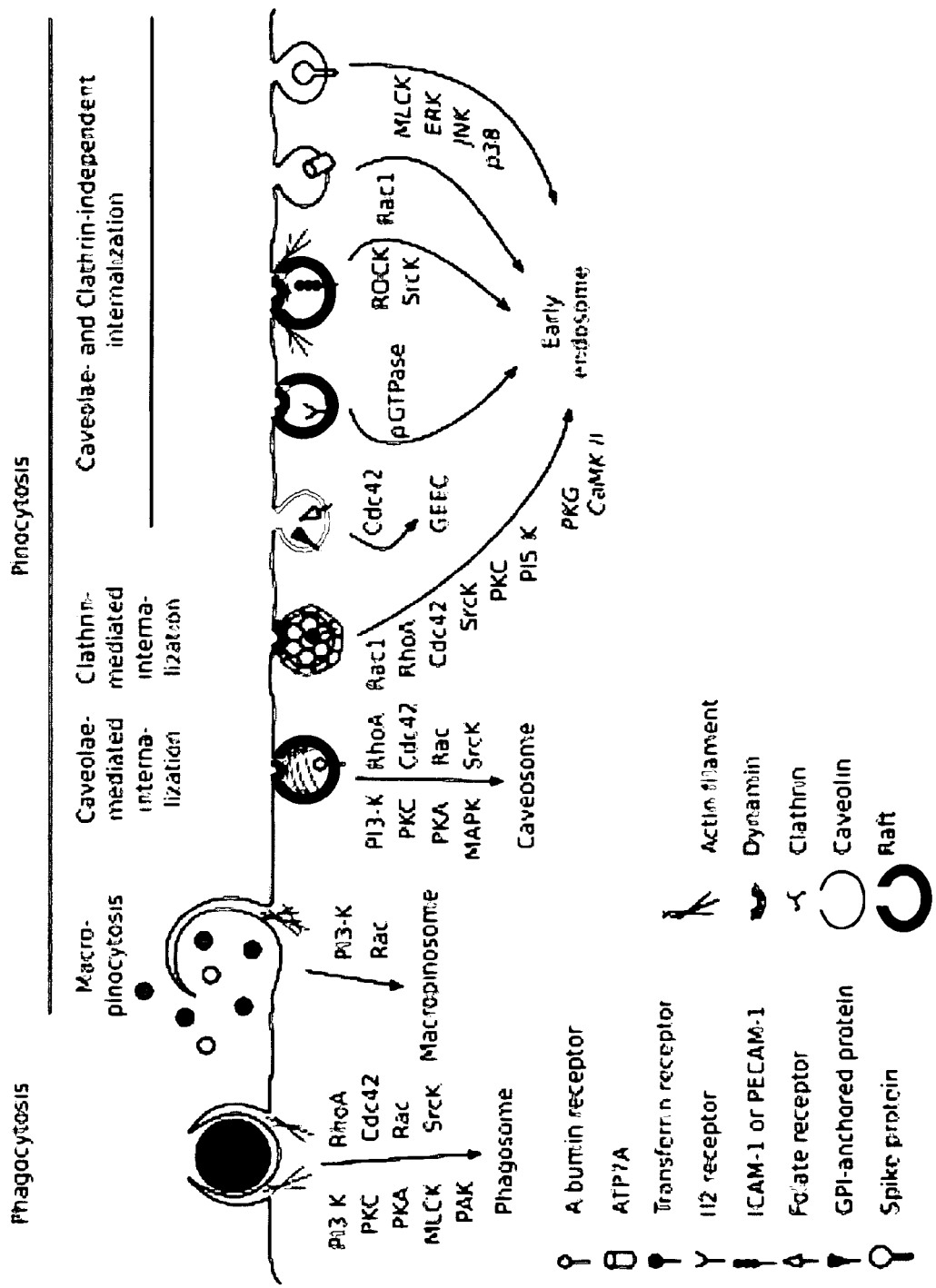
FIG. 1 Overview of the involvement of kinases and auxiliary Rho GTPase proteins during the different internalization pathways. The kinases in italic have been identified in this study. GPI: Glycosyl-phosphatidylinositol, GEEC: GPI-anchored protein-enriched early endosomal compartment.

Investigating the different internalization processes known and summarised in FIG. 1, it was found that the corona viral spike protein antigen-antibody complexes are internalized through a clathrin- and caveolae-independent pathway, which was also independent from rafts, rho-GTPases and actin. Myosin 1 and 6 were found to play a role in the internalization process, probably to guide the internalizing vesicles trough the actin barrier, and myosin 1 was also found to play a role in the intracellular trafficking of the vesicles over the microtubules.

Further characterization on the regulation of said pathway lead to the identification of a number of potential targets for the development of anti-corona viral therapies. As explained in more detail in the examples hereinafter, the internalization of surface expressed viral proteins (spike proteins) in FIPV infected cells is dependent on serine/threonine kinases but independent of tyrosine kinases and phosphatases. The kinase that was shown to positively regulate the internalization process is MLCK. As shown in the examples hereinafter, this characterization of MLCK as a positive regulator in the viral internalization process is not solely limited to the virus family of Coronaviridae. Also in representative examples of other virus families a specific MLCK inhibitor could prevent or reduce the internalization of virus particles in a host.

The target, i.e. the gene MLCK, according to the invention includes substantially identical homologues and variants of the nucleic acid molecules and expression products thereof, for example, molecules that are at least 10%, 20%, 30%, 40%, 50%, 55% or 60%, or at least 65%, 75%, 80%, 85%, 90%, or 95%, or as much as 96%, 97%, 98%, or 99% identical when optimally aligned at the amino acid or nucleotide level to the sequence of human MLCK (SwissProt entry Q15746; EMBL entry X90870).

The present invention is accordingly based on the validation of MLCK as a target in the development of therapies that interfere with the internalization of the virus in the viral host cell and in therapies that prevent the immune-evasion strategy of viruses to escape from the immune response of the host. Thus in a first aspect, the present to invention provides the use of MLCK as a target in the development of therapies, i.e. for the identification of compounds that prevent or reduce the internalization of viral proteins or of viral particles (viruses) in the host cell, including the internalization of membrane-bound viral proteins upon binding with virus specific antibodies, also known as the viral immune-evasion strategy. In particular to prevent the internalization, or immune evasion of viruses selected from the group consisting of Coronaviridae, such as for example feline infectious peritonitis virus (FIPV), feline enteric coronavirus (FECV), and Porcine respiratory coronavirus (PRCV); Nidovirales; Herpesviridae such as for example feline herpesvirus (FeHV), human herpes simplex virus 1 (HSV1), equine herpesvirus (EHV) and Pseudorabies virus (PrV); Arteriviridae such as for example Porcine reproductive and respiratory syndrome virus (PRRSV); Orthomyxoviridae such as for example Swine influenza virus; Retroviridae such as for example Human Immunodeficiency Virus 1 (HIV-1), and Flaviviridae such as for example hepatitis C virus (HCV); in particular to prevent the internalization, or immune evasion of Coronaviridae such as for example caused by the feline infectious peritonitis virus (FIPV); more in particular to prevent the internalization, or immune evasion of a virus selected from the group consisting of FIPV, FECV, PRCV, FeHV, HSV1, EHV, PrV, PRRSV, HIV and HCV; wherein said therapy comprises administering to the subject in need thereof, a MLCK inhibitor.

The methods to identify MLCK inhibitors, can be designed in many formats generally known in the art of screening compounds for biological activity of serine/threonine kinases, and include for example the monocyte internalization assay or the plaque reduction assay as provided in the examples hereinafter or an in vitro kinase assay wherein the serine/threonine kinase activity is determined by measuring phosphate incorporation in an appropriate substrate, such as for example the in vitro MLCK activity assay as described in Petrache I. et al., (2003).

It is thus an object of the invention to provide a method to identify compounds that prevent or reduce the internalization of viral proteins or of viral particles (viruses) in a host cell, said method comprising the step of contacting MLCK with the compound to be tested; and wherein a compound that inhibits MLCK activity is identified as a compound that prevents or reduces the internalization of viral proteins or of viral particles (viruses) in a host cell.

In a particular embodiment said screening method further comprises the step of contacting said host cell in the presence or absence of the compound to be tested with the viral particles or contacting said infected cells with specific antibodies and determine the internalization of said viral particles or said viral protein-antibody complexes in said host; wherein a compound that inhibits MLCK activity and reduces or prevents internalization of the viral proteins or viral particles in said host, is identified as a compound that reduces or prevents the internalization of viral proteins or of viral particles (viruses) in a host cell.

Any number of well-known methods for assaying endocytosis, such as for example described in Breiftfeld et al. J. Cell Biol. 109:475-486 (1989), may be used to determine the binding and internalization of the viral proteins or of the viral particles into the cell.

In a particular embodiment and as provided in the examples hereinafter, the internalization assays include the use of detectable antibodies specific for the viral particle or viral protein of interest. In said assays the degree of internalization is determined as an increase of the detectable label within the cells, and a compound capable to prevent or reduce said increase when compared to an untreated control is thus identified as a compound capable to prevent or reduce the internalization of viral proteins or of viral particles (viruses) in said host cell.

The term "detectable" refers to anything that allows the presence of the antibody to be detected. Any such molecule that allows for the detection of the antibody should have no effect on the affinity of the antibody for its target. The detectable polypeptide may be, by way of non-limiting example, a fluorescent polypeptide, a luminescent polypeptide, a visibly-colored polypeptide, a polypeptide with enzymatic activity, or a polypeptide capable of interacting with or binding to another molecule to produce a detectable product. In one particular embodiment, the label is one that requires no direct interaction or further sample processing for detectability, and thus is detectable by the application of exogenous methods such as absorbance of light, fluorescence, etc. In a more particular embodiment, the label is a fluorescent polypeptide. In another more particular embodiment, the label is green fluorescent protein and its polypeptide relatives.

Moreover, a plurality of detectable labels may be present in the antibodies used. For example, both a fluorescent label and an enzyme label may be appended in tandem to the C-terminus of an immunoglobulin heavy chain gene, such that the resulting expressed and assembled immunoglobulin molecule is detectable both by fluorescence and by histochemistry, by use of a fluorigenic and chromogenic/precipitating substrate of the enzyme, respectively. In another example, the antibody is detectable fluorometrically and by Western blot. Examples of polypeptides capable of being detected by enzymatic activity include various enzymes and catalytic polypeptide fragments thereof. Particularly preferred enzymatic labels include those which are able to produce a detectable color or fluorophore in a single step requiring a minimum or reagents, such as alkaline phosphatase, which can cleave a chromogenic substrate, such as p-nitrophenyl phosphate, or a fluorigenic substrate, such as ECF substrate (Amersham/Pharmacia); and a fluorigenic horseradish peroxidase substrate, FluoroBlot (Pierce Chemical Co.). Another example is a fluorescent beta-galactosidase substrate that can be used in live cells and is 100-fold more sensitive than GFP (Zlokarnik et. al., 1988, Science 279:85). The skilled artisan by the teachings herein will be amply aware of polynucleotides that may be fused to the immunoglobulin constant region(s) and upon expression produce an enzymatically-active fusion polypeptide comprising the immunoglobulin heavy and/or light chain.

Such labels may also result in the precipitation of a substrate, for histochemical localization of the antibody, or the label may interact with another detectable to component, and thus be, for example, a biotin-binding subunit of streptavidin or avidin, a His tag, a consensus sequence for biotinylation or a chitin-binding domain.

These particular examples of multiple labels on multiple sites of the antibodies are merely illustrative of the range of directly-labeled antibodies that the skilled artisan may be directed to prepare following the teachings herein, and any particular example or embodiment is not intended to be limiting whatsoever.

The "viral proteins" as used herein, generically refers to a protein generated by a virus, and primarily include structural proteins, forming the viral envelope and capsid, but also includes viral nonstructural proteins and viral regulatory and accessory proteins. Thus in a particular embodiment of the present invention, the viral proteins may be selected from any viral surface protein, including those surface proteins from enveloped viruses including retroviruses and coronaviruses and those from non-enveloped viruses such as capsid proteins, from for example adenoviruses.

The "viral particles" as used herein, refer to the whole virus with a central nucleosid, consisting of RNA or DNA, surrounded by a protein coat or capsid, found extracellularly and capable of surviving in crystalline form and infecting a living cell.

In those instances where the MLCK inhibitor, identified using the aforementioned assays and capable to prevent or reduce the internalization of viral proteins or of viral particles (viruses) in a host cell, is also capable to prevent or reduce viral infection, said MLCK inhibitor is further identified as an anti-viral compound.

Viral infection may be monitored by any suitable method. For example, death of host cells, viral replication, protein synthesis or the presence of viral protein on the surface of host cells may be monitored. Suitable methods for monitoring viral infection are described in Chesebro and Wehrly (1988), J. Virol. 62, 3779-3788 and in Pincus et al (1989), J. Immunol. 142, 3070-3075. HIV infection may be monitored using commercially available kits. For example, an HIV-I p24 ELISA (Coulter Inc, R&D Systems Inc.) or a RT-RCR kit for HIV long terminal repeat (LTR): NASBA [nucleic acid sequence-based amplification] (Amplicar (Roche Diagnostics)) may be used. Suitable assays are also described in the following documents: Steiger et al. (1991), J. Virol. Methods 34(2): 149-160, Byrne et al. (1998), Nucleic Acids Res. 16(9): 4165, Vandamme et al. (1995), J. Virol. Methods 52 (1-2): 121-132 and Bolton et al. (1987), J. Clin. Microbiol. 25(8): 1411-1415. HCV infection may be monitored using commercially available kits for the quantitative (Chiron bDNA signal amplification method) or qualitative (Cobas amplicor, Roche Diagnostics) RT-PCR for the 5' non coding region. Use of suitable assays are also described in Lunel et al. (1999), Hepatology 29(2): 528-535, Yeh et al. (1997), J. Virol. Methods 65(2): 219-226 and Jacob et al. (1997), Am. J. Clin. Pathol. 107 (3): 362-367. Viral infection may also be monitored by detection of viral load by PCR (polymerase chain reaction) such as for example RT-PCR tests from IDEXX for detection of Coronaviruses (FECV+FIP), Herpesvirus-1 and Equine Herpesvirus type 1 and 4. Influenza infection may be monitored using commercially available kits. For example the ELISA based QuickVue Influenza test from Quidel for the detection of influenza viruses.

As used herein, a "compound" is an organic or inorganic assembly of atoms of any size, and includes small molecules (less than about 2500 Daltons) or larger molecules, e.g. peptides, polypeptides, whole proteins and polynucleotides. Wherein, an inhibitor is a compound that reduces the serine/threonine kinase activity when assessed in the aforementioned assays and compared to the reference conditions thereof.

In a further aspect, the present invention provides the use of an MLCK inhibitor in therapies that interfere with the internalization of the virus in the viral host cell and in therapies that prevent or reduce the immune-evasion strategy of viruses to escape from the humoral immune response of the host. Said therapy comprising administering to said subject a MLCK inhibitor, in a therapeutically effective amount, i.e. an amount sufficient to prevent and/or reduce the internalization of a virus or of viral proteins in the viral host cells, more in particular in an amount sufficient to treat a viral infection in said subject. This amount varies inter alia, depending on the mode of administration, to the severity of the condition to be treated, and the concentration of the compound in the therapeutic formulation. Generally, an amount sufficient to treat a viral infection in said subject; will be determined on a case by case by an attending physician. In a particular embodiment, the MLCK inhibitor is used in the treatment of a viral infection and prevents in a first aspect the internalization of viral particles in the viral host cells, and in a second aspect the MLCK inhibitor prevents or reduces the internalization of membrane-bound viral proteins upon binding with antibodies in the cell. The MLCK inhibitor is particularly useful in the treatment of corona viral infections.

A subject or host (the viral infected subject) as used herein, is meant to include mammals, including humans, domestic and farm animals, such as dogs, horses, cats, cattle, pigs, sheep, etc. In particular cats, cattle, pigs and humans. As is known to the skilled artisan, a virus cannot reproduce on its own, i.e. without the assistance of host cells. The virus will enter these cells, introduce its own RNA or DNA into the nucleus and induce the production of replicates thereof. There is a plethora of potential host cells available in the organism and different viral types are specialized on different kinds of host cells. The influenza virus, for example, is using the cells lining the respiratory tract for reproduction, the virus causing poliomyelitis is using nerve cells and viral hepatitis is originating from the infection of liver cells and for HIV the main target is T-cells. Within the context of the present invention the term "host cells" includes any cells, including isolated cells such as the isolated monocytes and macrophages in the examples hereinafter, that allow viruses to enter said cells, introduce its own RNA or DNA into the nucleus of said cells and induce the production of replicates thereof.

The MLCK inhibitor used in said method of treatment, is meant to include any compound identified using the aforementioned methods and shown to act through the pathway described herein.

Particular examples of MLCK inhibitors include, but are not limited to ML-9, ML-7, staurosporine, KT-5926, Calphostin C, H-7, H-8, H-89, HA-100, HA-1 077, K-252a, K-252b, Piceatannol, fasudil, Peptide 18, Sm-I peptide, and Peptide 342-352, all functional equivalents, analogues, conjugates, and pharmaceutically effective derivatives thereof. Preferably, the MLCK inhibitor is ML-7 or K252a.

The compounds as mentioned herein above, can be administered as such but are typically administered as a pharmaceutical composition comprising said compounds and a pharmaceutically acceptable carrier.

These pharmaceutical compositions may be formulated and administered systemically or locally. Techniques for formulation and administration may be found in the latest edition of "Remington's Pharmaceutical Sciences" (Mack Publishing Co. Easton Pa.). Suitable routes may, for example, include oral or transmucosal administration as well as parenteral delivery, including intramuscular, subcutaneous, intramedullary, intrathecal, intraventricular, intravenous, intraperitoneal, or intranasal administration.

In a further embodiment, the compositions are in the form of food compositions. In certain embodiments, the composition is a cat food composition, further comprising in addition to the therapeutic agent (in particular an MLCK inhibitor), about 15% to about 50% protein, about 5% to about 40% fat, about 5% to about 40% carbohydrate, each on a dry weight basis, and having a moisture content of about 5% to about 20%. In certain embodiments, the foods are intended to supply complete necessary dietary requirements. Also provided are compositions that are useful as snacks, as nutrition bars, or other forms of food products or nutritional or dietary supplements, including tablets, capsules, gels, pastes, emulsions, caplets, and the like. Optionally, the food compositions can be a dry composition, a semi-moist composition, a wet composition or any mixture thereof. In one embodiment the food products are complete and nutritionally balanced, while in others they are intended as nutritional supplements to be used in connection with a well-balanced or formulated diet.

This invention will be better understood by reference to the Experimental Details that follow, but those skilled in the art will readily appreciate that these are only illustrative of the invention as described more fully in the claims that follow thereafter. Additionally, throughout this application, various publications are cited. The disclosure of these publications is hereby incorporated by reference into this application to describe more fully the state of the art to which this invention pertains.

EXAMPLES

The following examples illustrate the invention. They show that the internalisation of FIPV Ag-Ab complexes is dependent on MLCK activity and that the internalization and immune-evasion process of different viruses can be inhibited by ML-7, a MLCK inhibitor. Other embodiments will occur to the person skilled in the art in light of these examples.

Example 1

The Internalization of FIPV Ag-Ab Complexes is Dependent on MLCK Kinase Activity Material and Methods
Viruses and Antibodies A third passage of FIPV strain 79-1146 (American Type Culture Collection (ATCC)) on CrFK cells was used (McKeirnan et al., 1981). Polyclonal anti-FCoV antibodies were kindly provided by Dr Rottier (Utrecht University, The Netherlands). The antibodies were purified and biotinylated according to manufacturers instructions (Amersham Bioscience, Buckinghamshire, UK). FITC-labeled polyclonal anti-FIPV antibodies were purchased from Veterinary Medical Research and Development (VMRD, Pullman, Washington, USA). The monocyte marker DH59B, recognizing CD172a, was purchased from VMRD. Secondary antibodies and reagents: streptavidin Texas Red, streptavidin FITC and Phalloidin Texas Red were purchased from Molecular Probes (Molecular Probes-Invitrogen, Eugene, Oreg., USA).

Isolation and Inoculation of Blood Monocytes

Feline monocytes were isolated as described previously (Dewerchin et al., 2005). Cells were seeded on glass coverslips inserted in a 24-well dish (Nunc A/S, Roskilde, Denmark) in RPMI-1640 medium containing 10% fetal bovine serum (FBS), 0.3 mg/ml glutamine, 100 U/ml penicillin, 0.1 mg/ml streptomycin, 0.1 mg/ml kanamycin, 10 U/ml heparin, 1 mM sodium pyruvate, and 1% non-essential amino-acids 100× (GIBCO-Invitrogen, Merelbeke, Belgium). Non-adherent cells were removed by washing the dishes two times with RPMI-1640 at 2 and 24 hours after seeding. The adherent cells consisted for 86±7% of monocytes (as assessed by fluorescent staining with the monocyte marker DH59B). At 56 hours post seeding, monocytes were inoculated with FIPV at a multiplicity of infection (m.o.i.) of 5. Between 20 and 60 cells were analyzed per assay.

Internalization Inhibition Assays

Twelve hours after inoculation, monocytes seeded on glass coverslips were pre-incubated for 30 minutes at 37° C. with 5% CO2 in the presence of one of the following agents dissolved in RPMI: 300 nM staurosporine (Sigma-Aldrich GmbH), 10 mM sodium fluoride (Sigma-Aldrich GmbH), 50 µg/ml genistein (Sigma-Aldrich GmbH), 50 µM dephostatin (Calbiochem), 500 nM Bisindolylmaleimide (Calbiochem), 10 µM ML-7 (Calbiochem), 500 nM H-89 (Calbiochem), 3 µM KN-93 (Calbiochem), 200 µM PKG inhibitor (Calbiochem), 150 nM K-252a (Calbiochem), 0.45M sucrose (Sigma-Aldrich GmbH).

The working concentration of each reagent was based on literature values and was optimized qualitatively in internalization assays with control ligands (data not shown). Viability of the cells during the inhibition assay was tested for each inhibitor using ethidium bromide monoazide (Molecular Probes-Invitrogen) and was always over 99%. After pre-treatment, the cells were incubated with polyclonal biotinylated anti-FIPV antibodies in presence of one of the given inhibitors for 30 minutes at 37° C. Then, cells were fixed with 1% formaldehyde, permeabilized with 0.1% Triton X-100 (Sigma-Aldrich GmbH) and incubated with streptavidin-Texas Red for 1 hour at 37° C. Next, infected cells were visualized with polyclonal anti-FIPV-FITC. The glass coverslips were mounted on microscope slides using glycerin-PBS solution (0.9:0.1, vol/vol) with 2.5% 1,4-diazabicyclo)(2,2,2) octane (DABCO) (Janssen Chimica, Beerse, Belgium) and analyzed with confocal microscopy. Monocytes were scored as cells with fully internalized antigen-antibody complexes when no labeling could be observed at the plasma membrane. Percentages of cells with fully internalized complexes was calculated relative to the total amount of monocytes which showed antibody binding and thus had membrane expression before antibodies were added. Those monocytes constitute about 50% of the total amount of infected cells (Dewerchin et al., 2005). Because of the variability on the amount of cells with membrane expression, visualization of the complexes remaining at the plasma membrane was needed. Therefore, an acid washing step to remove the extracellular antibodies was not performed.

To test the effectiveness of all reagents, a suitable control was used in each experiment. Monocytes seeded on glass coverslips were pre-incubated for 30 minutes at 37° C. with 5% CO2 in the presence of one of the inhibitors. After treatment, the cells were incubated with biotinylated transferrin (Sigma-Aldrich GmbH) or fluorescent 1 µm polystyrene microspheres, FluoSpheres (Molecular Probes-Invitrogen), in presence of the inhibitor. Then, cells were fixed with 1% formaldehyde and permeabilized with 0.1% Triton X-100. The biotinylated transferrin was visualized by incubating the cells with streptavidin-FITC for 1 hour at 37° C. and cells incubated with fluorescent beads were incubated with phalloidin-Texas Red (Molecular Probes-Invitrogen) for 1 hour at 37° C. to visualize the lamellipodia. The glass coverslips were mounted on microscope slides using glycerin-DABCO and analyzed by confocal microscopy. For the controls, the monocytes were scored analogously as FIPV infected cells: ligands were considered "fully internalized" when they were only observed inside the cell. Fluorescent beads were considered internalized when they were found inside the cortical actin labeling.

Confocal Laser Scanning Microscopy

The samples were stained as described above and examined with a Leica TCS SP2 laser scanning spectral confocal system (Leica Microsystems GmbH, Wetzlar, Germany) linked to a DM IRB inverted microscope (Leica Microsystems). Argon and Helium/Neon laser lights were used to excite FITC (488 nm line) and Texas-Red (543 nm line) fluorochromes. The images were obtained with Leica confocal software and processed with the GIMP.

Statistical Analysis

Triplicate assays were compared using a Mann-Withney U test with SPSS11.0 (SPSS Inc., Chicago, WA). P values <0.05 were considered significantly different. For each assay, between 20 and 60 cells were counted.

Results

Figure 2:
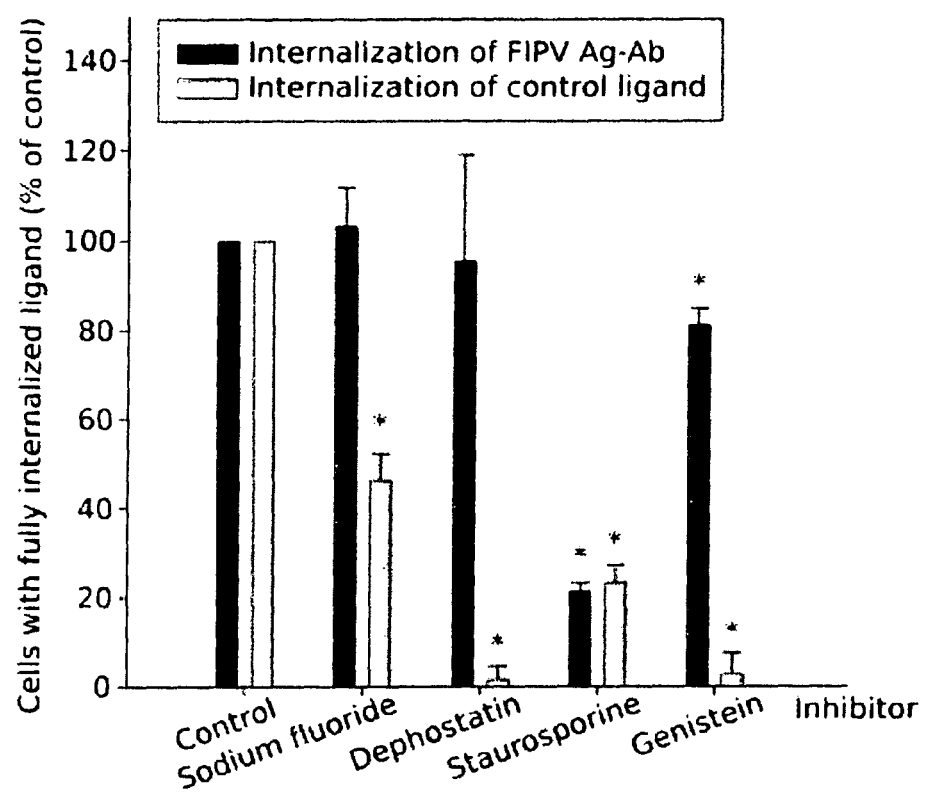

Internalization of Viral Antigens is Energy-Dependent and Regulated by a Serine/Threonine Kinase To obtain a first clue on the regulation of this internalization process, the importance of phosphorylation and/or dephosphorylation was tested with chemical inhibitors. Representative quantifications of the internalization assays in the presence of inhibitors are shown in FIG. 2.

Dephosphorylation. First, the importance of phosphatases for dephosphorylation was tested. Treatment with sodium fluoride (broad range phosphatase inhibitor) gave no reduction of internalization whereas the internalization of the control ligand transferrin amounted to 46±6% of the untreated control. In addition, treatment of cells with the more specific tyrosine phosphatase inhibitor, dephostatin, gave no reduction of internalized viral proteins either (96±23% of untreated control, in contrast to 2±3% for the control ligand beads). These results indicated that phosphatases do not play a role in antibody-induced internalization.

Phosphorylation. Next, it was investigated whether kinases played a role in internalization. Treatment of cells with the broad range serine/threonine kinase inhibitor staurosporine resulted in a reduction in viral protein internalization (21±2% of control) to a similar extent as for the control ligand, beads (23±4% of control). Using the tyrosine kinase inhibitor genistein, the internalization of viral antigens amounted to 81±4% of untreated control while the internalization of the control ligand albumin was 3±5% of the untreated control. The reduction in internalization caused by genistein was significant but small compared to the control ligand albumin.

This minor effect could be due to a non-specific action of the drug or it could be that tyrosine kinases play a role in the later stages of the internalization process, like intracellular transportation. Taken together, these data indicate an important role for (a) serine/threonine kinase(s) in the antibody-induced internalization of surface expressed viral proteins in FIPV infected monocytes.

Internalization of Viral Antigens is Regulated by Myosin Light Chain Kinase

Figure 3:
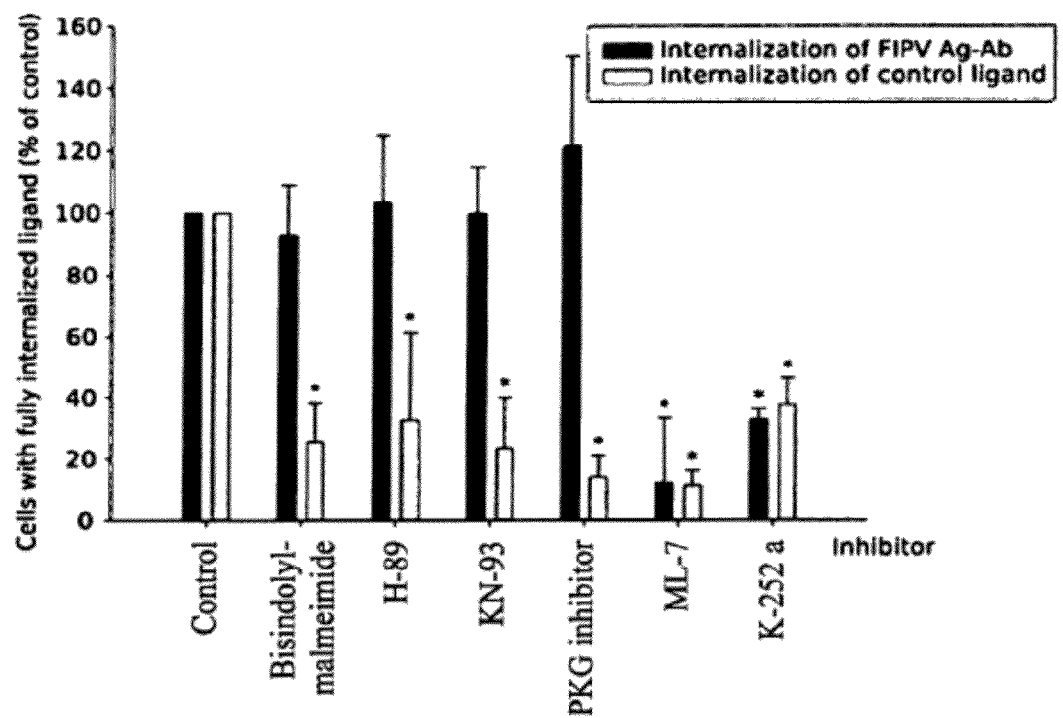
FIG. 3 Myosin light chain kinase (MLCK) inhibitors can block the internalization of surface expressed viral antigens in FIPV infected monocytes. A range of serine/threonine kinases were tested for their importance during the internalization process by using chemical inhibitors: Bisindolylmaleimide (PKC inhibitor), H-89 (PKA inhibitor), KN-93 (CaM-dependent kinase II inhibitor), PKG inhibitor, ML-7 (MLCK inhibitor) and K252-a (inhibits MLCK, PKA, PKC and PKG). Quantification of the internalization in feline monocytes after an internalization assays of 30 minutes using antibodies or control ligands, in the presence of the aforementioned inhibitors. Results are given relatively to a control of untreated cells. The black bars represent the internalization of the viral antigens. The grey bars represent the internalization of the control ligand (beads, transferrin or albumin). Data are means and standard deviations of triplicate assays. The asterisk marks results that are significantly different from the untreated control ($p<0.05$).

The serine/threonine kinases are the biggest group of kinases and consist of different classes among which: protein kinase C (PKC), protein kinase A (PKA) or cyclic AMP-dependent protein kinases, protein kinase G (PKG) or cyclic GMP-dependent protein kinases, the family of the calcium/calmodulin-dependent protein kinases (CaM K) and myosin light chain kinases (MLCK). The importance of these classes was tested by performing internalization assays in the presence of pharmacological inhibitors. The internalization of viral antigens remained unaffected in the presence of bisindolylmaleimide I (a PKC-inhibitor), H-89 (a PKA-inhibitor), KN-93 (a CaM K II-inhibitor) and PKG-inhibitor while the internalization of a control ligand was reduced to 25±13%, 33±29%, 23±16% and 14±7% respectively (representative results are given in FIG. 3). In contrast, the specific MLCK inhibitor ML-7, could inhibit the internalization of viral antigens to 12±21% of the untreated control and the uptake of beads, the control ligand, was equivalently reduced to 11±5% (FIG. 3). The importance of MLCK was confirmed by another MLCK inhibitor: K252a, which also inhibited the internalization of both the viral antigens as the control ligand (beads) to a similar level (FIG. 3). These results indicated that MLCK is required to enable the internalization of viral antigens.

Discussion

In FIPV infected monocytes, viral proteins are expressed in the plasma membrane in 50% of the cells (Dewerchin et al., 2005). Binding of FIPV-specific antibodies should enable the immune system of an infected cat to eliminate these monocytes. However, high antibody titers do not protect a cat against FIPV suggesting that FIPV possesses an immune evasion mechanism. We have shown that antibodies which bind to surface expressed proteins, cause the formed antigen-antibody complexes to internalize through a novel clathrin- and caveolae independent pathway, explaining why antibodies seem unable to mark infected cells for antibody-dependent cell lysis (Dewerchin et al., 2006, 2008b). In the current study, we wanted to elucidate how this new pathway is regulated.

Regulation of cellular processes generally involves signaling cascades in which proteins are activated or deactivated through phosphorylation and dephosphorylation by kinases and phosphatases, respectively. The amino acid residues at which phosphate groups can be added are tyrosine, threonine or serine. We already found that the internalization does not require phosphatidylinositol 3-kinase (inhibitor: wortmannin) nor Rho-GTPases (inhibitor: Toxin B) (Dewerchin et al., 2008b). The experiments presented here, showed that internalization occurred independent from serine/threonine and tyrosine phosphatases (inhibitors: sodium fluoride, dephostatin) and tyrosine kinases (inhibitor: genistein). However, the pathway was sensitive to the inhibitor staurosporine, indicating dependency on (a) serine/threonine kinase(s).

Serine/threonine kinases are the biggest group of kinases and consist of many different classes. Using chemical inhibitors, a potential role for protein kinase C (PKC), protein kinase A (PKA) or cyclic AMP-dependent protein kinases and for protein kinase G (PKG) or cyclic GMP-dependent protein kinases was investigated. Also two important members of the calcium/calmodulin-dependent protein kinases (CaMK) family were examined: CaMK II and myosin light chain kinase (MLCK). PKC is known to regulate Fc receptor-, complement receptor- and mannose receptor-mediated phagocytosis (Aderem and Underhill, 1999). PKA and MLCK were shown to mediate phagocytosis in neutrophils (Ydrenius et al., 2000). In our experiments, using primary monocytes, we could indeed block the phagocytosis of fluorescent beads in monocytes using the specific PKA, PKC and MLCK inhibitors. A link between PKG or CaMK II and internalization processes could not be found in literature, however, in our experiments, the uptake of transferrin could be blocked using the PKG inhibitor or the CaMK II inhibitor (KN-93). Since the transferrin receptor is internalized through clathrin coated vesicles, these tests indicate a possible role for PKG and CaMK II in clathrin mediated internalization.

Only MLCK was found to play a role in the internalization of surface expressed viral protein in FIPV infected monocytes. It has been described that MLCK co-localizes with cortical actin filaments and, in fibroblast cells, it is MLCK that phosphorylates myosin in the cell periphery while Rho kinase (ROCK) is responsible for phosphorylation of myosin in the cell center (Guerriero et al., 1981; Totsukawa et al., 2000). This complies with a possible role for MLCK in the internalization process. The confocal images (data not shown) show that the antigen-antibody complexes are maintained at or right under the plasma membrane when MLCK is inhibited (only 1 antigen-antibody complex has traveled further into the ML-7 treated monocyte, but chemical inhibitors can rarely block a cellular process by 100%). This is an indication that MLCK plays a role during the first steps of internalization (e.g. membrane remodeling) or during a subsequent step (e.g. trafficking through the cortical actin network). Different MLCKs have been characterized in several species. Sequence comparisons show that vertebrate skeletal muscle and smooth muscle MLCKs belong to two subfamilies derived from different genes (Gallagher et al., 1997). Skeletal muscle MLCKs are exclusively expressed in skeletal muscle, while smooth muscle MLCKs are ubiquitously expressed. Smooth muscle MLCKs are thus also active in non-muscle cells.

In literature it is stated that MLCK has a substrate specificity restricted to the regulatory light chain of myosin-II. However, most research has been done on muscle cells and MLCKs have been shown to function differently in non-muscle cells (Gallagher et al., 1997). So, it is possible that there are members of the MLCK family that are not restricted to myosin 2. The results presented here, show that MLCK is required for the internalization process. Considering the fact that in previous work, we have found that only myosin 1 and 6 are important during the internalization, and not myosin 2a nor 2b (nor myosin 5a, 7a, 9b and 10), this suggests the existence of a MLCK that regulates myosin 1 or 6.

In summary, it can be concluded that the internalization of surface expressed viral proteins in FIPV infected cells is dependent on serine/threonine kinases but independent of tyrosine kinases and phosphatases. The kinase that was shown to positively regulate the internalization process was MLCK.

Example 2

Internalization of Several Virus Types is Regulated by MLCK

Material and Methods
Plaque Reduction Assays

The antiviral potency of ML-7 was tested on the entry of the following viruses: feline coronavirus, porcine coronavirus, porcine arterivirus, feline herpesvirus, equine herpesvirus, herpes simplex virus 1 and swine influenzavirus, by checking to which degree the inhibitor is able to reduce the number of "Plaque Forming units" (PFU), or the number of infected cells (for feline coronavirus and porcine arterivirus). A PFU is a virus particle that is able to infect a cell and produce enough progeny viruses to infect surrounding cells. The antiviral potency of ML-7 on the entry of the feline coronavirus and porcine arterivirus in primary cells (monocytes and macrophages respectively), was determined by counting the number of single infected cells and not the plaques. These primary cells do not divide in vitro, and therefore they can not grow into a monolayer hence, plaques can not be formed.

1. Day 1

Cells were seeded in a 24-well plate at 300000 cells/ml. Carboxymethylcellulose (CMC) was prepared by adding 0,47 g CMC in 25 ml ultra pure water. This solution was then autoclaved.

2. Day 2

Cells were pretreated with a dilution series of the inhibitor ML-7 for 30 minutes at 37° C. (stock solution 10 mM). Table 1 shows the dilution series in which the amount of ML-7 was always taken from the previous dilution. Then, 10 µl virus was added to the cells at a concentration of 4000 PFU/ml and the plate was incubated for 1,5 h. After washing 3 times, 1 ml of CMC, which consisted of 50% CMC solution and 50% of double concentrated medium, was brought on the cells and the plates were further incubated at 37° C.

TABLE 1

Dilution series for ML-7

| Eppendorf | ML-7 (µl) | Medium (µl) | End concentration (µM) |
|---|---|---|---|
| 1 | 4 | 396 | 100 |
| 2 | 300 | 300 | 50 |
| 3 | 300 | 300 | 25 |
| 4 | 300 | 300 | 12.5 |
| 5 | 300 | 300 | 6.25 |
| 6 | 300 | 300 | 3.13 |
| 7 | 300 | 300 | 1.56 |
| 8 | 300 | 300 | 0.78 |

3. Day 3 or 4

After 24 hours (or 48 hours for FIPV strain Black and porcine respiratory coronavirus virus), the medium was removed and the plates were washed 3 times. Then the plates were dried by keeping them for 1 hour at 37° C., after which they were covered and kept at −20° C.

4. IPMA

The plates were adjusted to room temperature and the cells were fixed with formaldehyde (4%) for 10 minutes at room temperature. After washing 2 times, the cells were permeabilised with ethanol (containing 1% of $H_2O_2$). Then the cells were incubated for 1 hour at 37° C. with 200 µl of mouse monoclonal antibody recognising a viral protein and 10% negative goat serum (to reduce background). Cells were washed 2 times and then incubated for 1 hour with 200 µl of goat-anti mouse antibodies labeled with peroxidase. After washing 2 times, 200 µl of substrate was added (stock of substrate contains: 1 ml 3-amino-9-ethylcarbazole (AEC), 19 ml acetate buffer (pH 5) and 15 µl of $H_2O_2$). The substrate was incubated for 5 to 30 minutes, until the staining reaction was sufficient. Then, the reaction was stopped by removing the substrate and adding 500 µl of acetate buffer.

5. Analysis

The number of plaques was counted using an inverted light microscope. Then the number of plaques in the treated wells was normalized to the number of plaques in the control wells from that same repeat.

Single Infected Cell Reduction Assays

The single infected cell reduction assay was used to determine the antiviral potency of to ML-7 on the entry of hepatitis C virus (HCV).

1. Day 1

Huh7.5 hepatoma cells were seeded in a 96-well plate at 10000 cells/well in 100 µl medium containing 0, 2.5 or 25 µM of ML-7.

2. Day 2

Virus was diluted in medium containing the different concentrations of the inhibitor to reach an end concentration of $2,22.10^{\wedge}6$ IU/ml. 100 µl of this mixture was added to the wells and the plate was further incubated at 37° C.

3. Day 6

The cells were fixed and stained for NS5A (a HCV protein). Then the amount of HCV-positive clusters per well was counted. A cluster is defined as a group of positive cells that is separated from another cluster by at least 1 non-infected cell.

Results

The following paragraphs show the effect of the MLCK inhibitor ML-7 on the entry of different viruses.

Feline Coronaviruses

Figure 4:
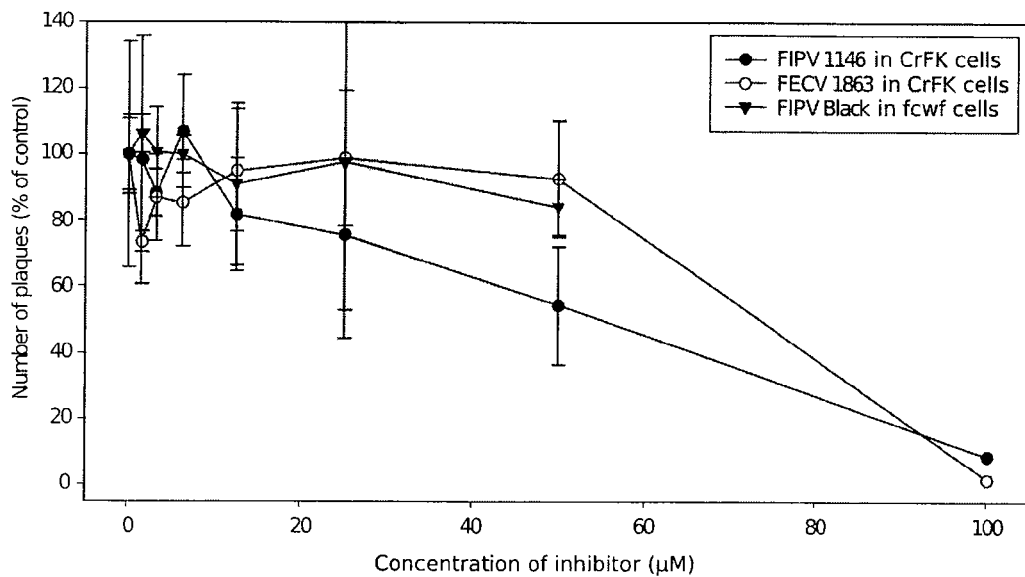
FIG. 4 The effect of the MLCK inhibitor ML-7 on the entry of the feline coronaviruses: FIPV 1146 (CrFK cells), FECV 1863 (CrFK cells) and FIPV Black (fcwf cells)

Feline coronaviruses belong to the family of the Coronaviridae and the order of the Nidovirales. FIG. 4 shows that ML-7 can reduce the entry of feline coronaviruses in vitro. A reduction to 88% of the control for FIPV on CrFK cells and to 73% for FECV on CrFK cells was seen at low concentrations of the inhibitor (3,13 en 1,56 µM respectively). This relatively limited effect could be due to the short pre-incubation period (30 minutes) with the inhibitor before the addition of the virus. Nevertheless, these findings indicate that MLCK is involved for the entry of feline coronaviruses and thus can be used as target for the development of antivirals.

At higher concentrations, the inhibitory effect seemed to be lost again. At the highest concentrations of 50 and 100 µM, the inhibitory effect increased rapidly. However, this effect might not be specific at these higher concentrations since it has been shown that ML-7 can also block protein kinase A and C at these concentrations (Saitoh et al., 1987). FIG. 4 also showed that there was little effect on the entry process of FIPV strain Black. This could be due to the fact that the experiment was done in another cell line (CrFK cells do not support the growth of serotype I FIPV strain such as the Black strain) and CrFK and fcwf cells could have different variants of MLCK.

Porcine Coronaviruses

Figure 5:
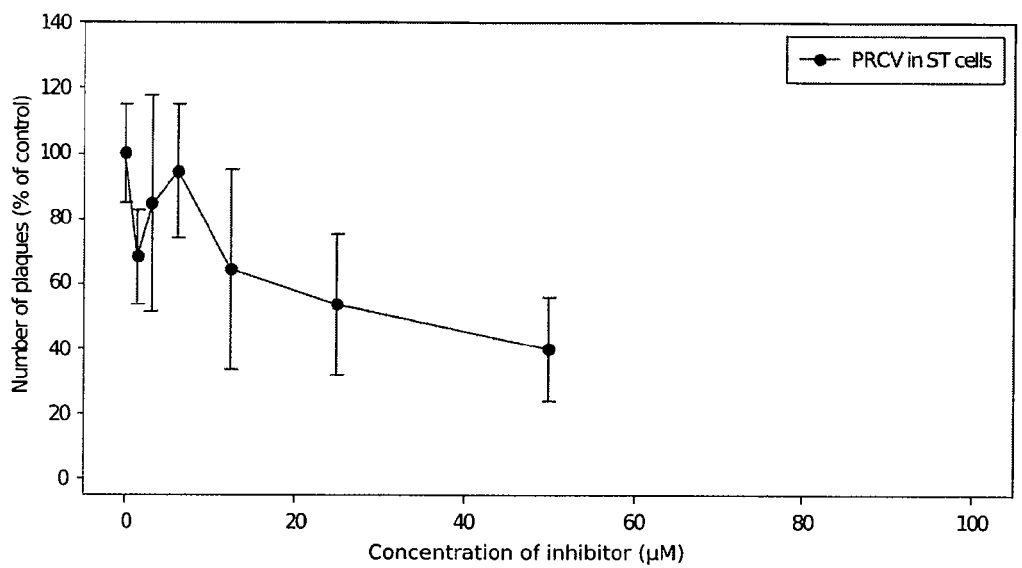
FIG. 5 The effect of the MLCK inhibitor ML-7 on the entry of the porcine coronavirus PCRV in ST cells FIG. 6 The effect of the MLCK inhibitor ML-7 on the entry of the porcine arterivirus PRRSV in MARC cells and macrophages FIG. 7 The effect of the MLCK inhibitor ML-7 on the entry of the herpesviruses FeHV (CrFK cells), HSV1 (VERO cells) and EHV (EEL cells)

Porcine respiratory coronavirus (PRCV) belongs to the family of the Coronaviridae and the order of the Nidovirales. FIG. 5 shows that the MLCK inhibitor ML-7 is able to reduce the entry of PRCV (and subsequent plaque formation) at a low concentration of 1,56 µM to 68% of the untreated control. Analogous to the feline coronaviruses, this inhibitory effect is lost again at higher concentrations (up to 6 µM). At even higher concentrations, the number of plaques is reduced again to reach about 40% of the untreated control at 50 µM. These results indicate that MLCK is also required for the entry of porcine coronaviruses.

Porcine Arteriviruses

Figures 6, 7:
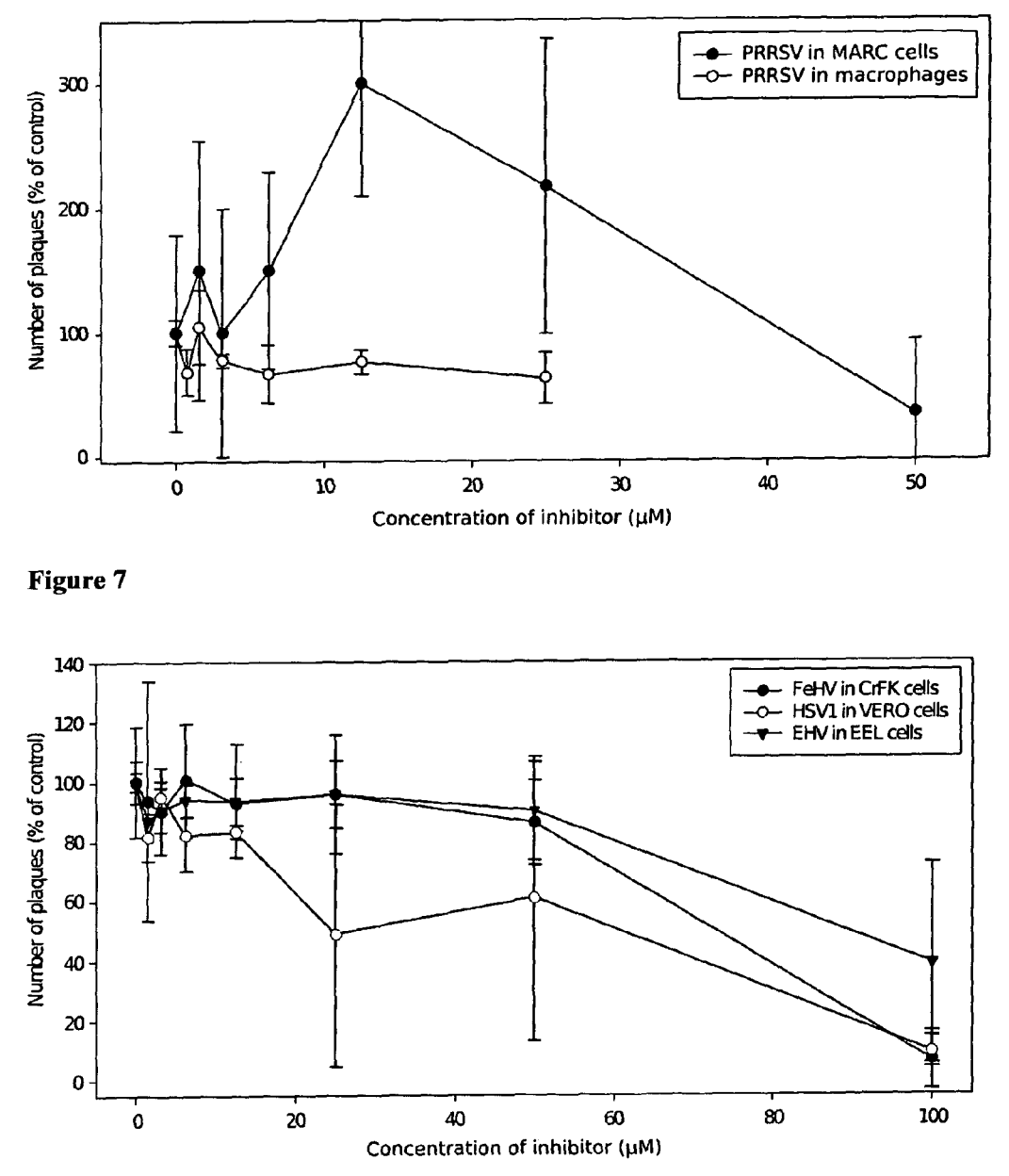

Porcine reproductive and respiratory syndrome virus (PRRSV) belongs to the family of the Arteriviridae, which together with the Coronaviridae constitutes the order of the Nidovirales. The tests were done in MARC cells and primary macrophages. The results in FIG. 6 show that in MARC cells, ML-7 seemed to have an activating effect instead of an inhibiting effect. This means that ML-7 might be an interesting additive in the production vessels of vaccine strains of PRRSV. On the other hand, when looking at the entry in the in vivo target cells of PRSSV, the alveolar macrophage, ML-7 was able to inhibit the entry of the virus at a low concentration (the number of plaques was reduced to 68% of the control at 0,78 µM of ML-7). There was no further reduction at the higher concentrations, indicating that the inhibitory effect was specific and limited to the effect on MLCK.

Herpesviruses

The effect of the MLCK inhibitor ML-7 was tested on the entry of feline herpesvirus (FeHV), human herpes simplex virus 1 (HSV1) and equine herpesvirus (EHV). These viruses belong the family of the Herpesviridae. The results in FIG. 7 show that there was some effect of the inhibitor at low concentrations. At 1,56 µM, the plaques were reduced to 79%, 81% and 86% of the untreated control for FeHV, HSV1 and EHV respectively. For HSV1 an additional effect was seen on 25 and 100 µM while for FeHV and EHV there was only an additional inhibitory effect at 100 µM. Similar to the previous experiments, it can be concluded that MLCK is also required for the entry of herpesviruses, albeit to a lesser extend.

Influenzaviruses

Figure 8:
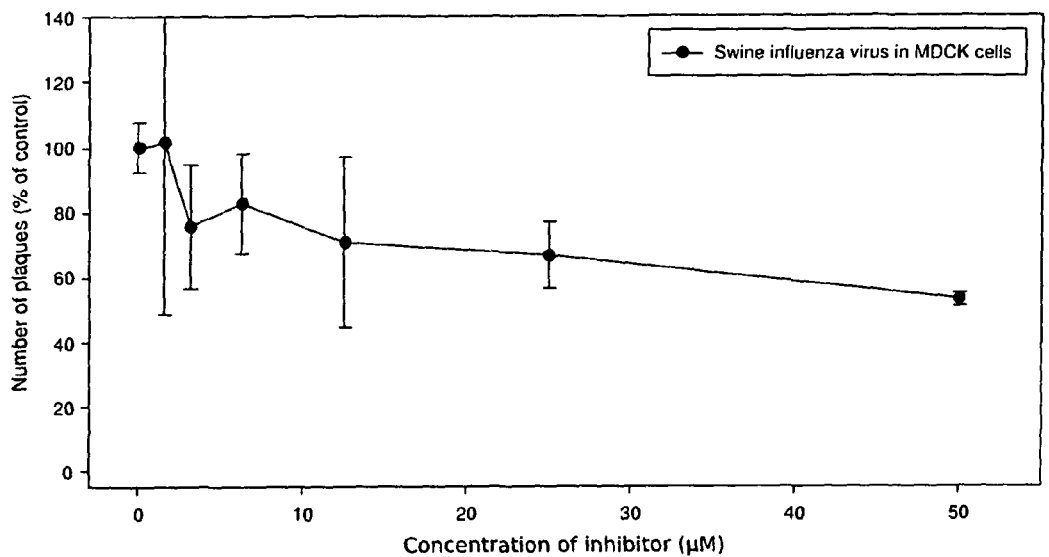
FIG. 8 The effect of the MLCK inhibitor ML-7 on the entry of the swine influenzavirus in MDCK cells FIG. 9 The myosin light chain kinase inhibitor ML-7 can block the antibody-induced internalization process of viral proteins in the plasma membrane of PrV infected porcine monocytes.

The effect of the MLCK inhibitor ML-7 was tested on the entry of swine influenzavirus. This virus belongs to the family of the Orthomyxoviridae. FIG. 8 shows that ML-7 was able to inhibit the entry of the virus at a low concentration (the number of plaques was reduced to 76% of the control at 3,13 µM of ML-7). There was no further reduction at the higher concentrations, indicating that the inhibitory effect was specific and limited to the effect on MLCK.

HCV

Figure 9:
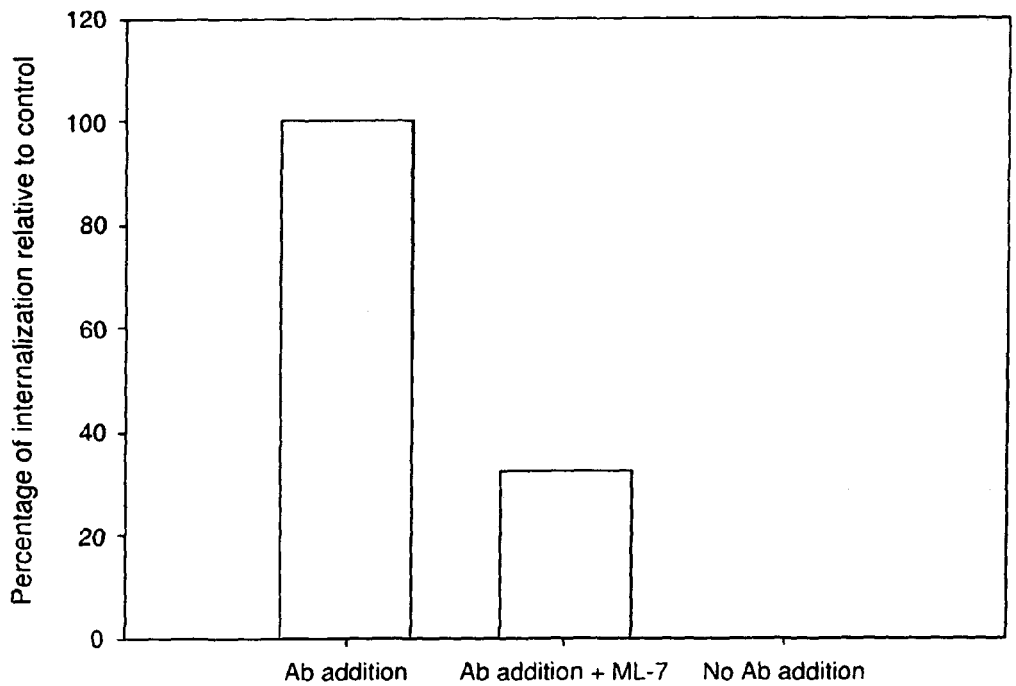

The effect of the MLCK inhibitor ML-7 was tested on the entry of human hepatitis C virus (HCV). This virus belongs to the family of the Flaviviridae. FIG. 9 shows that ML-7 was able to reduce the amount of infected clusters to 31% of the untreated control at 25 µM.

Example 3

Immune-Evasion of the Pseudorabies Virus is Dependent on MLCK

Pseudorabies virus (PrV) is a herpesvirus in pigs that is often used as a model for human herpes simplex virus infections. When porcine monocytes (the in vivo target cells) are infected with PrV, viral proteins are expressed at the plasma membrane. Upon addition of virus specific antibodies, the formed antigen-antibody complexes are internalized in the cell. This is an immune-evasion process by which the infected cells can hide themselves from the immune system of the host. Here, it was tested if MLCK is required for this process.

Materials and Methods

Porcine monocytes were pre-treated with 10 µM of ML-7 for 30 minutes. Then, FITC labeled anti-PRV polyclonal antibodies were added and the cells were incubated at 37° C. for 1 hour. Finally, the cells were fixed, mounted on microscope oslides and analyzed with fluorescence microscopy. For the controls, the internalization assay was performed in the absence of the inhibitor or in the absence of antibodies. The results were put relatively to the untreated control.

Results

Figure 10:
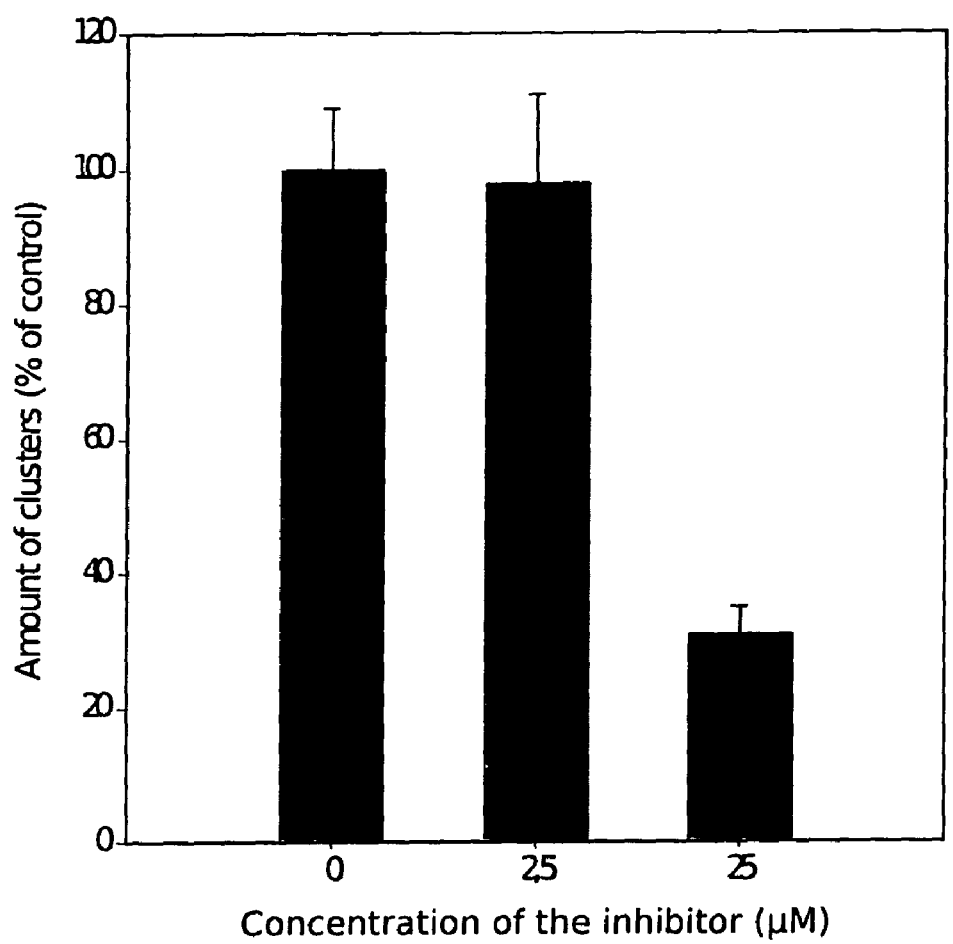
FIG. 10 The effect of the MLCK inhibitor ML-7 on the entry and spread of hepatitis C virus FIG. 11 SupT1 cells infected with HIV-1 NL4.3-eGFP at different dilutions (10-1000×) in the presence of different concentrations (0-25 µM) of ML-7 inhibitor. Percentage of eGFP cells measured by FACS at day 3 post infection.

FIG. 10 shows that antibody-induced internalization of PrV viral proteins in porcine monocytes can be inhibited by ML-7, indicating that MLCK is required in this immune-evasion process. Therefor for PrV, a porcine herpesvirus, MLCK can serve as a target for the development of an antiviral agent that is directed against the immune-evasion process of internalization.

Example 4

Effect of an MLCK Inhibitor on HIV1

Introduction

In this experiment the Human Immunodeficiency Virus 1 (HIV-1) strain HIV-1 NL4.3-eGFP which is a lab strain with an eGFP reporter, was used to infect the human T-cell lymphoblatic lymphoma cell line SupT1. The percentage of eGFP positive cells measured at different time point was used as endpoint read out SupT1. ML-7 inhibitor was used at three different concentration: 0 (DMSO), 2,5 and 25 µM.

Experimental Design

1. Day 0

SupT1 cells were at a concentration of 20000 cell/well in 200 µl of iMDM medium supplemented with 10% FCS, 1% penicillin/streptomycin and 1% L-glutamine, and were centrifuged at 300 g for 5 min at 4° C. Supernatant was removed and the cells were treated for 30 min with 100 µl of 0 (DMSO at 1/200 dilution in culture medium), 5 and 50 µM ML-7 inhibitor prepared in culture medium at 1/2000 and 1/200 dilution respectively. Meanwhile, HIV-1 NL4.3-eGFP virus was diluted in 10 fold dilution series in a separate plate (starting from 1/5 of stock, put on first well). 100 µl of each virus at every dilution was transferred to the corresponding well of the culture plate treated with the inhibitor. Four hours later approximately 100 µl was transferred to an U-bottom plate and was frozen at −80° C. This sample served to measure p24 input virus on time 0.

2. Day 3

Cells were centrifuged at 300 g for 5 min at 4° C. and approximately 100 µl was collected then stored at −80° C. for p24 measurement. Then 100 µl of cells infected with HIV1-NL4.3-eGFP virus was collected for the determination of the percentage of eGFP positive cells by FACS. Cells were resuspended in 200 µl of medium containing the adequate ML-7 inhibitor concentration.

3. Day 7

Cells were treated in the same way as in day 3

During the course of the experiment cells were monitored carefully by microscopy to check for signs of infection such as:

eGFP expression

Syncytia formation

Cell death

Results

Figure 11:
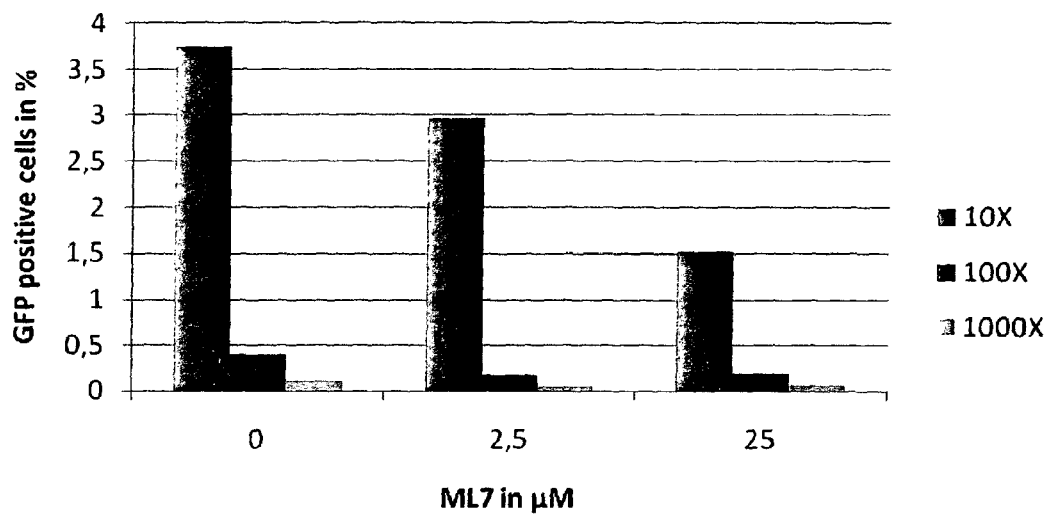
Figure 12:
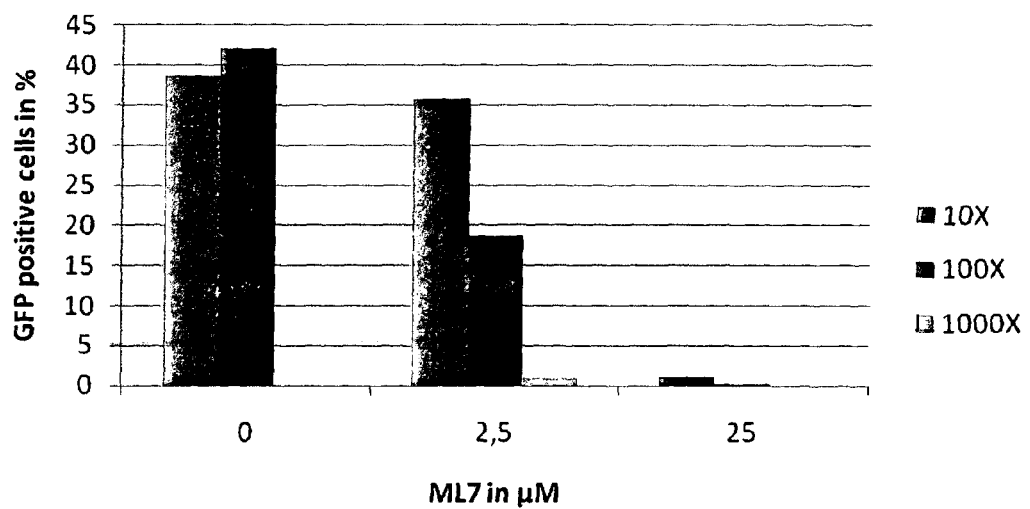
FIG. 12 SupT1 cells infected with HIV-1 NL4.3-eGFP at different dilutions (10-1000×) in the presence of different concentrations (0-25 µM) of ML-7 inhibitor. Percentage of eGFP cells measured by FACS at day 7 post infection.

ML-7 induces a strong inhibition of HIV-1 NL4.3-eGFP infection in SUPT1 cells. Both at 3 days post inoculation (FIG. 11) and at 7 days post inoculation (FIG. 12), a low ML-7 concentration of 2.5 µM has a clear effect on the HIV infection, the latter being more pronounced in the 100× virus dilution. At the higher ML-7 concentration of 25 µM, the effect of the virus dilution is lost (see the tables hereinafter).

| | SupT1 NL4.3 | | | | | | |
|---|---|---|---|---|---|---|---|
| | ML-7 in µM (Day 3) | | | | ML-7 in µM (Day 7) | | |
| Virus Dil | 0 | 2.5 | 25 | Virus Dil | 0 | 2.5 | 25 |
| 10X | 3.75 (100%) | 2.98 (80%) | 1.52 (41%) | 10X | 38.7 (100%) | 35.8 (92%) | 1.13 (3%) |

-continued

| | SupT1 NL4.3 | | | | | | |
|---|---|---|---|---|---|---|---|
| | ML-7 in μM (Day 3) | | | | ML-7 in μM (Day 7) | | |
| Virus Dil | 0 | 2.5 | 25 | Virus Dil | 0 | 2.5 | 25 |
| 100X | 0.39 (100%) | 0.18 (46%) | 0.19 (49%) | 100X | 42.1 (100%) | 18.64 (44%) | 0.14 (0.3%) |
| 1000X | 0.11 (100%) | 0.04 (36%) | 0.06 (54%) | 1000X° | 0.03 (100%) | 0.95 (3160%)° | 0.06 (200%) |

°observed variability at 1000X dilution is due to the fact that these values are at or below the detection limit of the assay.

At high concentration ML-7 also inhibited completely virus induced syncytia (data not shown). Finally ML-7 protected SupT1 cells from virus mediated cell death at 25 μM concentration. This protective effect was mild with the intermediate inhibitor concentration. No toxic effect of ML-7 on cells was evident. By contrast non treated cells were all dead by day 7 at 10 and 100 times diluted virus.

Conclusion

ML-7 inhibits HIV entry and spread in SupT1 cells

References

Aderem, A. and Underhill, D. (1999). Mechanisms of phagocytosis in macrophages. Annu Rev Immunol, 17:593-623.

Dewerchin, H., Cornelissen, E., and Nauwynck, H. (2005). Replication of feline coronaviruses in peripheral blood monocytes. Arch Virol, 150(12):2483-2500.

Dewerchin, H., Cornelissen, E., and Nauwynck, H. (2006). Feline infectious peritonitis virus-infected monocytes internalize viral membrane-bound proteins upon antibody addition. J Gen Virol, 87:1685-1690.

Dewerchin, H., Cornelissen, E., Van Hamme, E., and Nauwynck, H. (2008a). Microtubules, actin and myosins cooperate during internalization and trafficking of antigen-antibody complexes in feline infectious peritonitis virus infected monocytes. manuscript in preparation.

Dewerchin, H., Cornelissen, E., Van Hamme, E., Smits, K., Verhasselt, B., and Nauwynck, H. (2008b). Viral proteins in feline infectious peritonitis virus infected monocytes are internalized through a clathrin- and caveolae-independent pathway. J Gen Virol, submitted.

Gallagher, P., Herring, B., and Stull, J. (1997). Myosin light chain kinases. J Muscle Res Cell Mot, 18:1-16.

Guerriero, V., Rowley, D., and Means, A. (1981). Production and characterization of an antibody to myosin light chain kinase and intracellular localization of the enzyme. Cell, 27:449-458.

Kim Young-Sook and Kawai Akihiko, 1998 Biol. Pharm. Bull 21 (5) 498-505

McArdle, F., Bennet, M., Gaskell, R., Tennant, B., Kelly, D., and Gaskell, C. (1992). Induction and enhancement of feline infectious peritonitis by canine coronavirus. Am J Vet Res, 53:1500-1506)

McKeirnan, A., Evermann, J., Hargis, A., and Ott, R. (1981). Isolation of feline coronaviruses from 2 cats with diverse disease manifestations. Feline Practice, 11(3):16-20.

Pedersen, N. and Boyle, J. (1980). Immunologic phenomena in the effusive form of feline infectious peritonitis. Am J Vet Res, 41:868-876

Pedersen, N. and Black, J. (1983) Attempted immunization of cats against feline infectious peritonitis using either avirulent virus or subletal amounts of virulent virus. Am J Vet Res, 44:229-234

Petrache I. et al., The FASEB Journal 2003, 17: 407-416.

Saitoh, M., Ishikawa, T., Matsushima, S., Naka, M., Hidaka, H. (1987) Selective inhibition of catalytic activity of smoothe muscle myosin light chain kinase. J Biol Chem, 262: 7796-7801

Totsukawa, G., Yamakita, Y., Yamashiro, S., Hartshorne, D., Sasaki, Y., and Matsumura, F. (2000). Distinct roles of ROCK (Rho-kinase) and MLCK in spatial regulation of MLC phosphorylation for assembly of stress fibers and focal adhesions in 3T3 fibroblasts. J Cell Biol, 150:797-806.

Vennema, H., de Groot, R., Harbour, D., Dalderup, M., Gruffydd-Jones, T., Horzinek, M., and Spaan, W. (1990a). Early death after feline infectious peritonitis challenge due to recombinant vaccinia virus immunization. J Virol, 64:1407-1409

Ydrenius, L., Majeed, M., Rasmusson, B., Stendahl, O., and Sarndahl, E. (2000). Activation of cAMP-dependent protein kinase is necessary for actin rearrangements in human neutrophils during phagocytosis. J Leukoc Biol, 67:520-528.

---

The invention claimed is:

1. A method for identifying compounds that reduce the internalization of viral proteins or viruses into a host cell, comprising contacting myosin light chain kinase (MLCK) with the compound to be tested; wherein a compound that inhibits MLCK activity is identified as a compound that reduces the internalization of viral proteins or viruses into said host cell.

2. The method according to claim 1 comprising contacting a host cell in the presence of the compound to be tested with the viral proteins or viruses wherein a compound that inhibits (MLCK) activity and/or reduces the internalization of viral proteins or of viruses into said host cell is identified as a compound that reduces the internalization of viral proteins or viruses into said host cell.

3. The method according to claim 2, wherein said host cells is contacted with virus specific antibodies.

4. The method according to claim 1, wherein the viral proteins or viruses are derived from a virus selected from the group consisting of Coronaviridae, Arteriviridae, Herpesviridae, Orthomyxoviridae, and Flaviviridae.

5. A method for reducing the internalization of viral proteins or of viruses into the host cells of a subject with a viral infection, said method comprising administering to said subject an effective amount of a myosin light chain kinase (MLCK) inhibitor or a pharmaceutical composition comprising a MLCK inhibitor.

6. The method according to claim 5 wherein the MLCK inhibitor reduces a viral infection.

7. The method according to claim 6 wherein the viral infection is caused by a virus selected from the group consisting of Coronaviridae, Arteriviridae, Herpesviridae, Orthomyxoviridae, and Flaviviridae.

8. The method according to claim 5 wherein the MLCK inhibitor is selected from the group consisting of ML-9, ML-7, staurosporine, KT-5926, Calphostin C, H-7, H-8, H-89, HA-100, HA-I 077, K-252a, K-252b, Piceatannol, fasudil, Peptide 18, Sm-I peptide, and Peptide 342-352, and all functional equivalents, analogues, conjugates, and pharmaceutically effective derivatives thereof.

* * * * *